(12) United States Patent
Knausdorf et al.

(10) Patent No.: US 10,576,754 B2
(45) Date of Patent: Mar. 3, 2020

(54) SYSTEM AND METHOD FOR VERIFYING THE CURE OF ULTRAVIOLET CURABLE MATERIALS IN A THREE-DIMENSIONAL 3D OBJECT PRINTER

(71) Applicant: Xerox Corporation, Norwalk, CT (US)

(72) Inventors: Peter J. Knausdorf, Henrietta, NY (US); Jack T. LeStrange, Macedon, NY (US); Anthony S. Condello, Webster, NY (US); Mandakini Kanungo, Penfield, NY (US); Xin Yang, Webster, NY (US)

(73) Assignee: Xerox Corporation, Norwalk, CT (US)

(*) Notice: Subject to any disclaimer, the term of this patent is extended or adjusted under 35 U.S.C. 154(b) by 410 days.

(21) Appl. No.: 15/608,089

(22) Filed: May 30, 2017

(65) Prior Publication Data
US 2018/0345562 A1  Dec. 6, 2018

(51) Int. Cl.
| | | |
|---|---|---|
| *B41J 3/407* | (2006.01) | |
| *B41J 3/00* | (2006.01) | |
| *G01N 21/956* | (2006.01) | |
| *G01N 21/00* | (2006.01) | |
| *G01N 21/27* | (2006.01) | |

(52) U.S. Cl.
CPC ............ *B41J 3/4073* (2013.01); *B41J 3/00* (2013.01); *G01N 21/00* (2013.01); *G01N 21/27* (2013.01); *G01N 21/956* (2013.01)

(58) Field of Classification Search
CPC .......... B41J 3/4073; B41J 3/00; G01N 21/27; G01N 21/00; G01N 21/956
See application file for complete search history.

(56) References Cited

U.S. PATENT DOCUMENTS

| | | |
|---|---|---|
| 6,923,115 B1 | 8/2005 | Litscher et al. |
| 7,765,931 B2 | 8/2010 | Kennedy, III et al. |
| 9,114,282 B2 | 8/2015 | Kennedy, III |
| 9,120,300 B2 | 9/2015 | Moehringer et al. |
| 2002/0097280 A1 | 7/2002 | Loper et al. |
| 2005/0178279 A1 | 8/2005 | Valls |
| 2006/0230969 A1* | 10/2006 | Vosahlo ............... B41J 11/002 101/488 |
| 2009/0256897 A1 | 10/2009 | Polk et al. |
| 2011/0012952 A1 | 1/2011 | Chang et al. |
| 2013/0189503 A1* | 7/2013 | Kozee ............... C09D 11/328 428/195.1 |
| 2014/0313267 A1* | 10/2014 | Fassam ............... B41M 7/0081 347/102 |
| 2017/0100898 A1 | 4/2017 | Colter et al. |

FOREIGN PATENT DOCUMENTS

EP          2432639 A1    11/2010

* cited by examiner

*Primary Examiner* — Justin Seo
(74) *Attorney, Agent, or Firm* — Maginot Moore & Beck LLP

(57) ABSTRACT

A direct-to-object printer includes an ultraviolet (UV) curing verification subsystem. The verification subsystem includes a ribbon that frictionally engages an image on an object that contains UV curable material. An imaging device generates image data of the ribbon that engaged the image and the image data is processed to determine whether any uncured UV material is present on the ribbon.

21 Claims, 4 Drawing Sheets

SYSTEM AND METHOD FOR VERIFYING THE CURE OF ULTRAVIOLET CURABLE MATERIALS IN A THREE-DIMENSIONAL 3D OBJECT PRINTER

TECHNICAL FIELD

This disclosure relates generally to a system for printing on three-dimensional (3D) objects, and more particularly, to systems that print on objects with ultraviolet (UV) curable materials.

BACKGROUND

Commercial article printing typically occurs during the production of the article. For example, ball skins are printed with patterns or logos prior to the ball being completed and inflated. Consequently, a non-production establishment, such as a distribution site or retail store, for example, in a region in which potential product customers support multiple professional or collegiate teams, needs to keep an inventory of products bearing the logos of various teams popular in the area. Ordering the correct number of products for each different logo to maintain the inventory can be problematic.

One way to address these issues in non-production outlets is to keep unprinted versions of the products, and print the patterns or logos on them at the distribution site or retail store. Printers known as direct-to-object (DTO) printers have been developed for printing individual objects. Some of these printers use UV curable materials to form images on the objects. UV curable materials require a UV radiation source that directs UV light onto the materials on the object surface. This light cures the materials and helps eliminate vapors that otherwise emanate from the materials. Some of these vapors may be noxious to humans and non-reacted components may irritate human skin.

To avoid issues that can arise from UV curable materials that have not been completely cured, the images formed with these materials are typically tested for the completeness of their cure. One way of testing the curing of these materials is to have a person rub the image on the object with a cloth or swab containing a solvent, such as isopropyl alcohol. If the material is not fully cured, then some of the uncured material rubs off and can be observed on the cloth or swab. While this method is effective, it does possess some problems. For one, the testing person can be exposed to the vapors from the uncured UV material or the person's skin may be irritated by non-reacted components. Additionally, because the method is performed by hand, the techniques of the testers differ and those differences can affect the results of the tests. This method can also be time-consuming because it is performed by humans and it is not integral to the printing of the objects. An automated method for verifying the curing of UV curable materials would be beneficial.

SUMMARY

A new three-dimensional (3D) object printing system enables the cure of UV materials in an image on a printed object to be verified as part of the printing process. The printing system includes a plurality of printheads, each printhead in the plurality of printheads being configured to eject marking material, a first member having a first end and a second end, the plurality of printheads being positioned between the first end and the second end of the first member, a holder configured to hold an object and to move along the member between the first end and the second end of the first member, a first actuator operatively connected to the holder, the actuator being configured to move the holder along the first member to enable the object to move past the printheads and receive marking material from the printheads in the plurality of printheads and form an image on the object, an ultraviolet (UV) curing device configured to emit UV light, the UV curing device being positioned between the plurality of printheads and the second end of the member to enable the UV curing device to cure UV material ejected onto the object in the holder by at least one printhead in the plurality of printheads, an UV curing verification subsystem having a ribbon that is positioned to engage the image on the object as the holder moves past the UV curing verification subsystem, and an imaging device configured to generate image data of the ribbon after the ribbon has engaged the image on the object, and a controller operatively connected to the plurality of printheads, the first actuator, the UV curing device, and the imaging device of the UV curing verification subsystem. The controller is configured to operate the first actuator to move the holder and object along the first member in a process direction, to operate the plurality of printheads to eject marking material onto the object and form the image on the object, to operate the UV curing device to direct UV light onto the image on the object, to receive image data of the ribbon from the imaging device, and to identify whether any marking material from the image is on the ribbon.

A UV material cure verification subsystem verifies the curing of UV curable images before the object exits a printer. The subsystem includes a ribbon, a member positioned to support a portion of the ribbon to enable an image on an object containing UV curable material to frictionally engage the ribbon portion supported by the member, and an imaging device configured to generate image data of the ribbon after the ribbon has engaged the image on the object.

BRIEF DESCRIPTION OF THE DRAWINGS

The foregoing aspects and other features of a printing system and UV material cure verification subsystem that verifies the curing of UV curable materials on objects in the printer are explained in the following description, taken in connection with the accompanying drawings.

DETAILED DESCRIPTION

Figure 1:
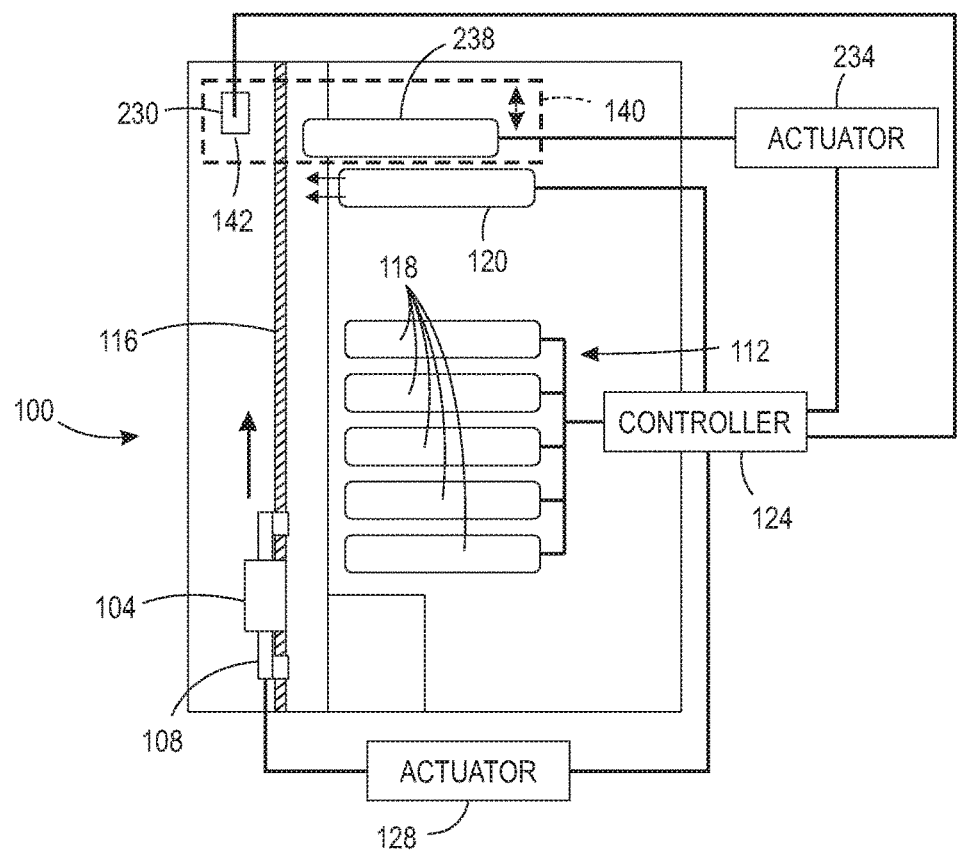
FIG. 1 is a schematic diagram of a side view of a printing system having a UV curing verification subsystem that verifies the curing of UV materials on objects in the printer before the objects leave the printer.

For a general understanding of the present embodiments, reference is made to the drawings. In the drawings, like reference numerals have been used throughout to designate like elements.

FIG. 1 depicts a direct-to-object (DTO) printing system 100 configured to print the surface of an object 104 mounted to a holder 108 as the holder 108 moves in a process direction indicated by the arrow on a member 116 past an array of printheads 112. As used in this document, "process direction" refers the direction of movement of an object past the printheads in a printer and "cross-process direction" refers to an axis that is perpendicular to the process direction in a plane parallel to the plane in which the holder of the object is moving. If one or more of the printheads 118 in the array 112 ejects ultraviolet (UV) material, then the UV curing device 120 is operated by controller 124 to cure the UV material. The controller 124 is also configured to operate the actuator 128 to move the holder 108 along the member 116 after the object is mounted into the holder. Controller 124 is configured to operate the printheads 118 in the array 112 to eject marking material onto the surface of the object 104 and controller 124 operates the UV curing device 120 selectively to direct UV light onto the image formed on an object. As used in this document, "UV light" refers to light having a wavelength that is shorter than visible light, but longer than X-rays. The wavelength of such light is about 10 nm to about 400 nm.

With continued reference to FIG. 1, after the image on the object has been exposed to the UV light produced by the UV curing device, the holder continues along the member 116 to a position opposite a UV curing verification subsystem 140. The controller 124 operates the actuator 128 to stop the holder and the object at the subsystem 140 to enable the subsystem to verify whether the UV curable materials in the image on the object were fully cured. After the subsystem has tested the image on the object and determined whether the UV curable material was fully cured, then the controller 124 operates the actuator 128 to move the holder 108 to an access area where an operator can remove the object from the holder. The subsystem generates a signal at the access area that indicates whether the material was fully cured or not. If it was not fully cured, then the operator discards the object. Otherwise, the operator places the object in inventory or processes it for checkout. As used in this document, the word "subsystem" refers to two or more components that are operated to perform a particular function within a larger system.

In the printer 100, the subsystem 140 includes an imaging device 230 and an image tester 238. The image tester 238 is configured to engage the image on the object 104 with a material having a solvent that releases uncured UV material from the image onto the material. The imaging device 230 generates image data of the material and this image data is provided to the controller 124, which processes the image data to determine whether uncured UV material is present on the material containing solvent. In the embodiment depicted in FIG. 1, the image tester 238 is configured for movement between a first position, which is between the UV curing device 120 and the imaging device 230, and a second position that is opposite the imaging device 230. An actuator 234 is operatively connected to the image tester 238 to move the tester between the first position and the second position and the controller 124 is operatively connected to the actuator 234 to operate the actuator for that purpose. In this embodiment, the holder 108 offsets the object 104 from the member 116 and the image tester is offset from the member 116 so it can engage the object. Likewise, the imaging device 230 is offset from the member 116 so it can generate image data of the material in the image tester 238 that engaged the object 104.

Figure 2:
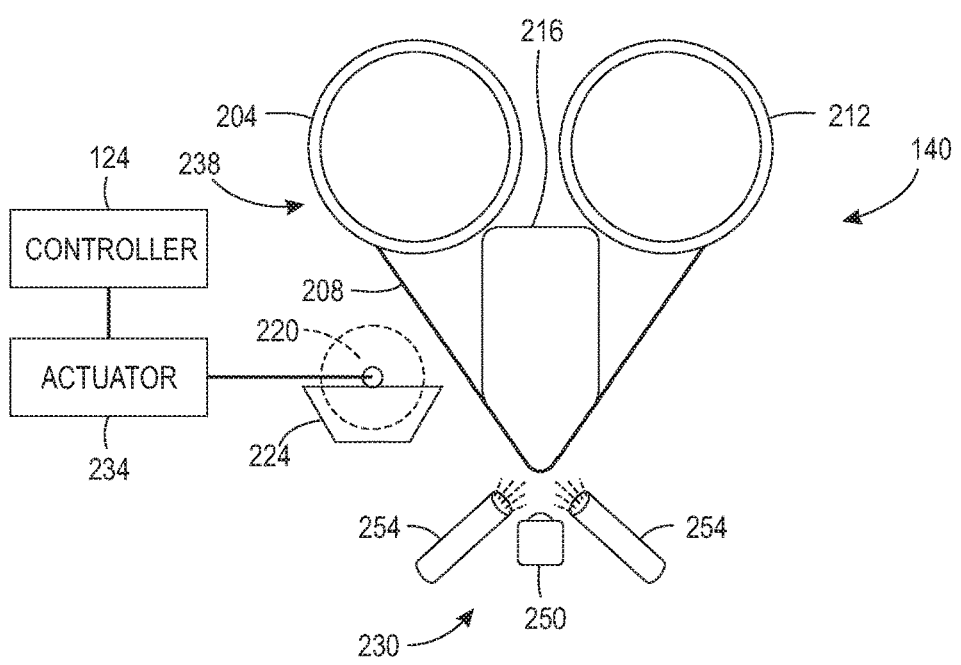
FIG. 2 depicts a first embodiment of the UV curing verification subsystem that can be used in the system of FIG. 1.

FIG. 2 is an illustration of a first embodiment of the UV curing verification subsystem 140 that can be used in the printing system 100. The image tester 238 of the subsystem 140 includes a spool 204 around which a supply of ribbon 208 is wrapped. One end of the ribbon extends to a take-up reel 212. Between the spool 204 and the take-up reel 212 is a member 216 with a rounded end, which is called a stylus in this document, that engages the ribbon 208. Other member shapes are possible for performing the purpose of the stylus 216, which is to keep the ribbon taunt between the spool and reel, and to provide a backing for frictionally engaging an object with the ribbon. As used in this document, "ribbon" means a material sufficiently absorbent that it can receive and hold a solvent and can receive and hold UV material released from an image on an object by the solvent. The ribbon can be any suitable material, such as a fabric made of cotton, nylon, or polyester, but the ribbon material needs to be compatible with the solvent used with the ribbon. For example, polyester and isopropyl alcohol are not compatible with one another, but cotton could be used with isopropyl alcohol and polyester with another suitable solvent. The ribbon can be impregnated with the solvent so the ribbon leaves the spool 204 containing the solvent. Alternatively, a supply of solvent can be provided within the stylus 216 or supplied to the stylus 216 from an external source to apply the solvent to the ribbon 208. Another alternative for supplying solvent to the ribbon is a metering roller 220, which can be partially submerged in a sump 224 of the solvent and rotated to apply the solvent to the ribbon. An actuator 234 operated by the controller 124 moves the roller 220 into engagement with the ribbon 208 to apply the solvent and then returns the roller to the sump. Alternatively, the metering roller 220 can have an internal supply of solvent stored within the inner volume of the roller. The roller is configured to enable the solvent to seep out from the supply with the inner volume and migrate to the surface of the roller.

The imaging device 230 includes an image data generator 250 and one or more light sources 254. The image data generator 250 can be a photometric device, such as a digital camera implemented with CMOS or CCD sensors, or an illuminance meter. Alternatively, the image data generator 250 can be a radiometric device. As used in this document, "photometric device" refers to an instrument configured to generate data corresponding to luminance parameters for visible light. As used in this document, "digital camera" means a device having a plurality of sensors, each of which generates data corresponding to a luminance intensity of light impinging on the sensor. As used in this document, "illuminance meter" means a device that measures predominately visible light (380 to 780 nanometers), but may have some tapering sensitivity at the ultraviolet and near infrared wavelengths. As used in this document, "radiometric device" means an instrument configured to generate data corresponding to radiometric parameters for light in the infrared, visible, and ultraviolet portions of the light spectrum.

When the subsystem 140 is in the first position, an object having an image that was cured by the UV curing device 120 can contact the ribbon 208 held against the stylus 216 as the actuator 128 moves the object past the stylus 216. This movement can include operating the actuator 128 to move the object bidirectionally against the ribbon 208 on the stylus 216. This frictional contact between the ribbon and the image on the moving object is sufficient to remove a portion of any uncured UV curable material in the image. Alternatively, the object and the image can be moved to engage the ribbon 208 at the stylus 216 and the actuator 234 is operated to move the tester 238 bidirectionally to rub the ribbon 208 against the object 104. In yet another alternative embodiment, an actuator 242 is operatively connected to spool 204 and take-up reel 212. In this embodiment, the holder and object are stopped opposite the stylus 216 so the ribbon 208 frictionally engages the object surface. The controller 124 then operates the actuator 242 to move the ribbon bidirectionally to rub the surface of the object with the ribbon 208 to obtain a sample of any uncured material. Then either the tester 238 is moved to be opposite the imaging device 230 for imaging of the ribbon or the object 104 is moved away from the stylus 216 so the imaging device 230 can be moved opposite the stylus for imaging of the ribbon.

After the image frictionally engages the ribbon 208 to enable uncured material sampling, the object is held stationary opposite the first position of the subsystem 140 and the actuator 234 is operated to move the tester 238 to the second position to enable the imaging device 230 of the subsystem 140 to generate image data of the ribbon on the stylus 216. In an alternative embodiment, the controller 124 operates the actuator 128 to reverse the movement of the holder 108 and the object 104 and then operate another actuator, such as actuator 234, to move the imaging device 230 opposite the ribbon at the proper focal distance for imaging the ribbon at the end of the stylus 216. After the ribbon is imaged, the controller 124 operates the actuator to retract the imaging device 230 for testing of another object. As shown in FIG. 2, the image data generator 250 is a digital camera configured to receive light reflected by the ribbon from two light sources 254. The light sources 254 generate light in the visible portion of the light spectrum that is directed towards the ribbon 208 on the stylus 216. Light reflected by the ribbon and any UV material on the ribbon is received by the image data generator 250, which generates image data of the ribbon. This generated image data is provided to the controller 124 for processing.

The controller 124 processes the image data from the different types of imaging devices differently. For digital camera photometric devices, image data for a clean ribbon can developed empirically and stored in a memory operatively connected to the controller or image data for a clean ribbon can be identified with reference to areas of the ribbon that do not contact the image when the object is rubbed against the ribbon. The image data for areas contacting the image can then be compared to an average value of the clean ribbon image data as a threshold. Any image data differing from this threshold by a predetermined amount indicates that uncured UV material has rubbed onto the ribbon. For illuminance meter imaging devices, empirically determined image data for various colors of UV materials are stored in a memory operatively connected to the controller. The controller compares image data received from the illuminance meter imaging device to the image data values for the various colors and any received image data values that are within a predetermined range of the stored image data values are identified as corresponding to the color associated with the stored image value. The presence of color on the ribbon indicates that UV material from the image on the object has rubbed onto the ribbon. Processing image data from radiometric imaging devices is similar to the processing of digital camera photometric devices except the measurements are related to radiance rather than luminance parameters.

Figure 3:
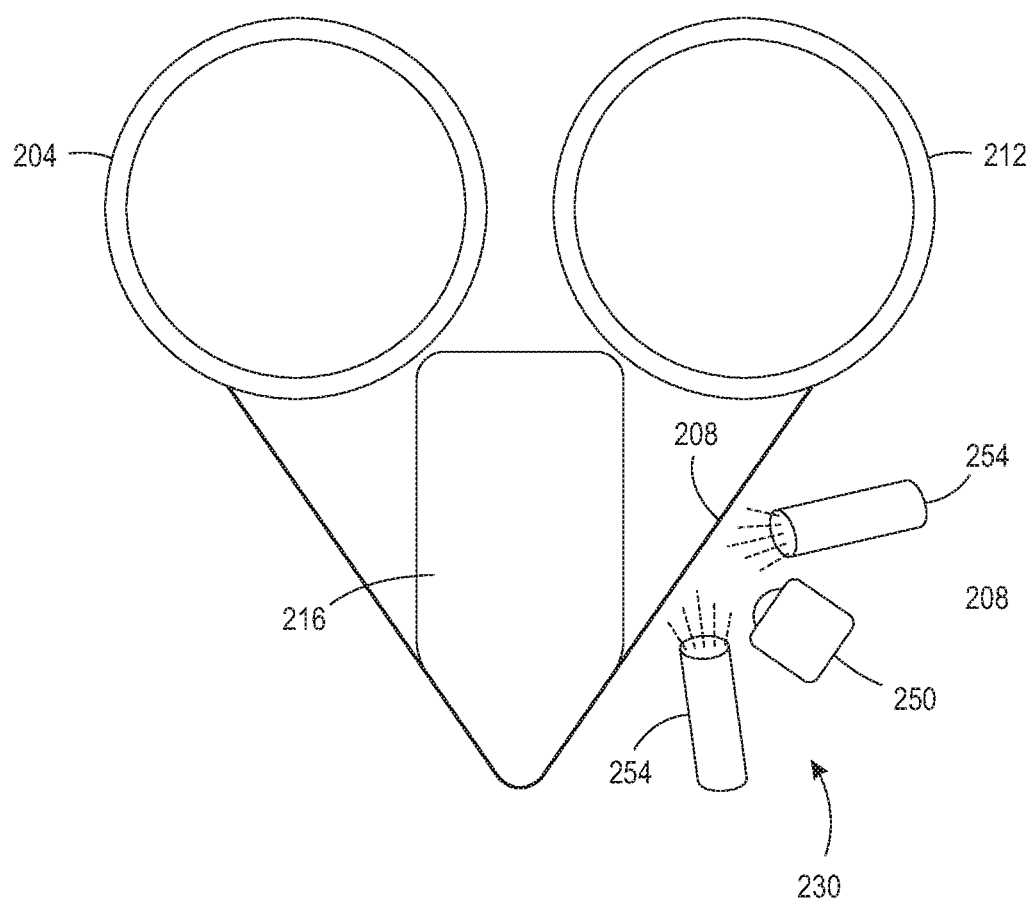
FIG. 3 depicts a second embodiment of the UV curing verification subsystem that can be used in the system of FIG. 1.

FIG. 3 depicts an alternative embodiment of subsystem 140. In this embodiment, the image device 230 is positioned between the take-up reel 212 and the end of the member 216 that backs the ribbon 208 while the object 104 engages the ribbon. Again, the light source 254 is located on the same side of the ribbon 208 as the image data generator 250, whether the image data generator is a photometric device or a radiometric device. The advantage of this embodiment is that neither the subsystem 140 nor the imaging device 230 need be configured for movement since the ribbon that engages the object passes the imaging device 230 even while the object remains at the end of the stylus 216 so the image data can be generated with the object at that position. The controller processes the image data as described above to determine whether the UV material has been properly cured.

Figure 4:
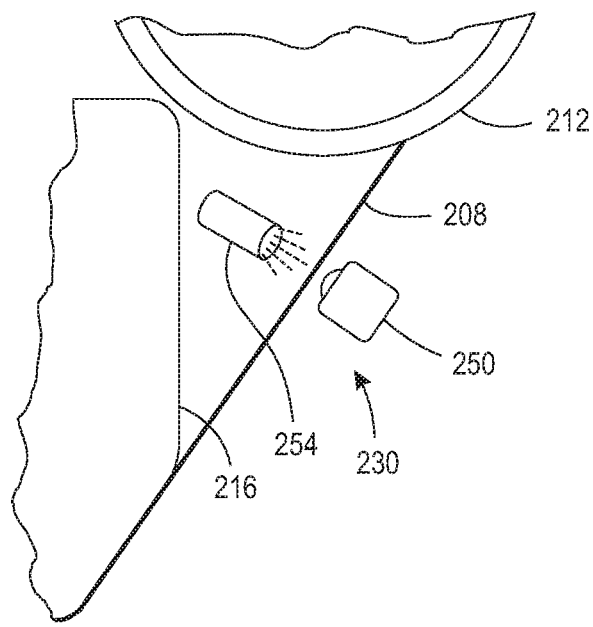
FIG. 4 depicts a third embodiment of the UV curing verification subsystem that can be used in the system of FIG. 1.
Figure 5:
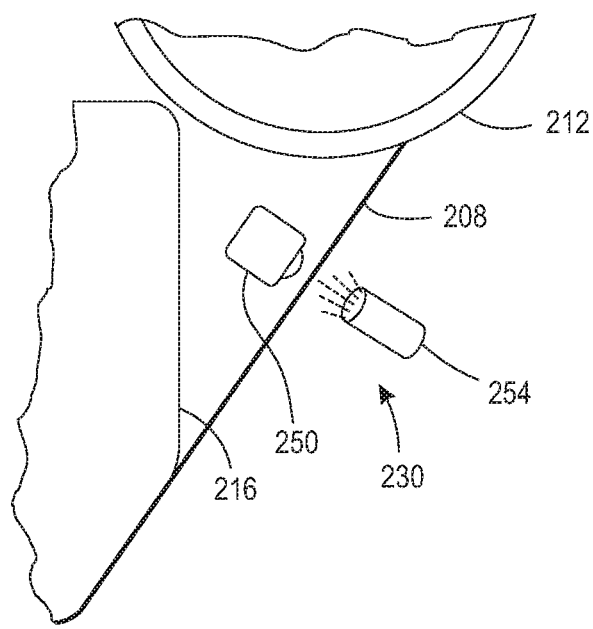
FIG. 5 depicts a fourth embodiment of the UV curing verification subsystem that can be used in the system of FIG. 1.

Another embodiment of the subsystem 140 is shown in FIG. 4. In this embodiment, the imaging device 230 is configured for a view of the ribbon 208 that receives light that has been transmitted through the ribbon 208 before it reaches the image data generator 250, which can be a photometric device or a radiometric device. These image data are processed as described above except the empirically determined image data used for a threshold or for color detection are identified from light transmitted through a clean ribbon rather than from light reflected from a clean ribbon. FIG. 5 shows an alternative embodiment in which the positions of the image data generator 250 and the light source 254 are reversed. The principles of operation for this embodiment are the same as those described with reference to FIG. 4.

Figure 6:
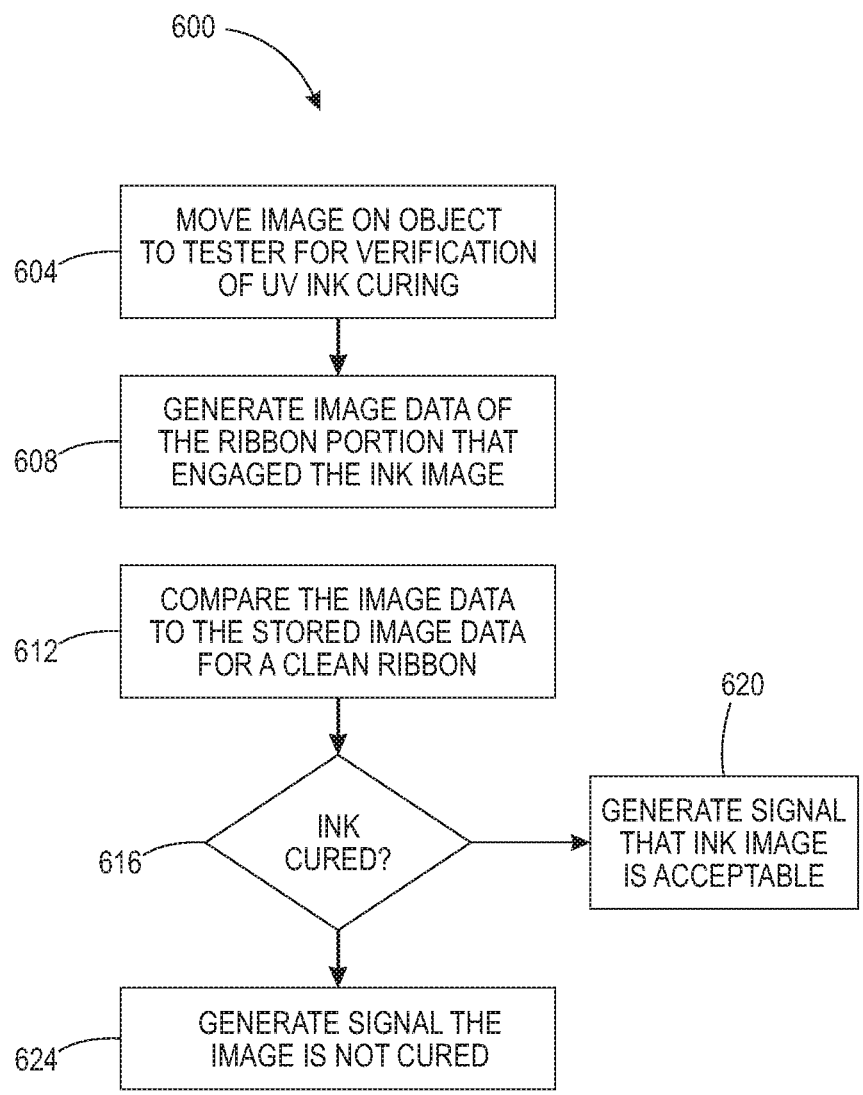
FIG. 6 is a flow diagram for a process of operating a printer that verifies the curing of UV material in an image formed by the printer.

A process for operating the printer 100 is shown in FIG. 6. In the description of the process, statements that the process is performing some task or function refers to a controller or general purpose processor executing programmed instructions stored in non-transitory computer readable storage media operatively connected to the controller or processor to manipulate data or to operate one or more components in the printer to perform the task or function. The controller 124 noted above can be such a controller or processor. Alternatively, the controller can be implemented with more than one processor and associated circuitry and components, each of which is configured to form one or more tasks or functions described herein. Additionally, the steps of the method may be performed in any feasible chronological order, regardless of the order shown in the figures or the order in which the processing is described.

FIG. 6 is a flow diagram of a process 600 that implements the verification of UV material curing described above. The process 600 begins by operating actuator 128 to move an object held by the holder 108 past the subsystem 140 to rub an image containing UV material on the object against the ribbon 208 at the end of stylus 216 (block 604). That portion of the ribbon is imaged by imaging device 230 (block 608) and the data are compared to the data stored in the printer to identify whether UV material has been rubbed onto the ribbon (block 612). If no UV material is detected (block 616), then a signal is generated that the object is acceptable for use once it is moved to a position for removal from the printer (block 620). Otherwise, a signal is generated to indicate the object is to be discarded when it is moved to the position for removal from the printer (block 624). The object is discarded, rather than being further cured, because the image has been smeared by the testing and would require both reprinting and re-curing with the likelihood that the image quality would suffer from the underlying marred image. The signals for an acceptable or unacceptable article can be a message or indicator light illumination on a user interface operatively connected to the controller 124.

It will be appreciated that variations of the above-disclosed apparatus and other features, and functions, or alternatives thereof, may be desirably combined into many other different systems or applications. Various presently unforeseen or unanticipated alternatives, modifications, variations, or improvements therein may be subsequently made by those skilled in the art, which are also intended to be encompassed by the following claims.

What is claimed is:

1. A printing system comprising:
   a plurality of printheads, each printhead in the plurality of printheads being configured to eject marking material;
   a first member having a first end and a second end, the plurality of printheads being positioned between the first end and the second end of the first member;
   a holder configured to hold an object and to move along the member between the first end and the second end of the first member;
   a first actuator operatively connected to the holder, the actuator being configured to move the holder along the first member to enable the object to move past the printheads and receive marking material from the printheads in the plurality of printheads and form an image on the object;
   an ultraviolet (UV) curing device configured to emit UV light, the UV curing device being positioned between the plurality of printheads and the second end of the member to enable the UV curing device to cure UV material ejected onto the object in the holder by at least one printhead in the plurality of printheads;
   an UV curing verification subsystem having a ribbon that is positioned to engage the image on the object as the holder moves past the UV curing verification subsystem, and an imaging device configured to generate image data of the ribbon after the ribbon has engaged the image on the object; and
   a controller operatively connected to the plurality of printheads, the first actuator, the UV curing device, and the imaging device of the UV curing verification subsystem, the controller being configured to operate the first actuator to move the holder and object along the first member in a process direction, to operate the plurality of printheads to eject marking material onto the object and form the image on the object, to operate the UV curing device to direct UV light onto the image on the object, to receive image data of the ribbon from the imaging device, and to identify whether any marking material from the image is on the ribbon.

2. The printing system of claim 1, the imaging device of the UV curing verification subsystem further comprising:
   an image data generator; and
   at least one source of visible light configured to direct light toward the ribbon.

3. The printing system of claim 2 wherein the image data generator is a photometric device.

4. The printing system of claim 3 wherein the photometric device is a digital camera.

5. The printing system of claim 3 wherein the photometric device is an illuminance meter.

6. The printing system of claim 2 wherein the image data generator and the at least one source of visible light are on opposite sides of the ribbon to enable light from the at least one source of visible light to pass through the ribbon and be received by the image data generator.

7. The printing system of claim 2 wherein the image data generator and the at least one source of visible light are positioned on a same side of the ribbon to enable light from the at least one source of visible light to be reflected from the ribbon into the image data generator.

8. The printing system of claim 6, the UV curing verification subsystem further comprising:
   a spool of ribbon;
   a take-up reel;
   a second member positioned between the spool of ribbon and the take-up reel, a portion of the ribbon extending from the spool of ribbon to an end of the second member and continuing to the take-up reel; and
   the image data generator and the at least one source of visible light being positioned on the same side of the ribbon between the end of the second member and the take-up reel.

9. The printing system of claim 8 further comprising:
   a second actuator operatively connected to one of the imaging device and the UV curing verification subsystem, the second actuator being configured to move the imaging device or UV curing verification subsystem operatively connected to the second actuator between a first position that enables the image on the object to engage the ribbon and a second position that enables the at least one light source of the imaging device to illuminate the ribbon and the image data generator of the imaging device to generate image data of the ribbon.

10. An ultraviolet (UV) curing verification subsystem comprising:
    a ribbon;
    a member positioned to support a portion of the ribbon to enable an image containing UV curable material to frictionally engage the ribbon portion supported by the member, the image being on an object; and
    an imaging device configured to generate image data of the ribbon after the ribbon has engaged the image on the object.

11. The UV curing verification subsystem of claim 10 further comprising:
    a controller operatively connected to the imaging device, the controller being configured to receive image data of the ribbon from the imaging device and to identify whether any UV curable material from the image is on the ribbon.

12. The UV curing verification subsystem of claim 11, the imaging device further comprising:
    an image data generator; and
    at least one source of visible light configured to direct light toward the ribbon.

13. The UV curing verification subsystem of claim 12 wherein the image data generator is a photometric device.

14. The UV curing verification subsystem of claim 13 wherein the photometric device is a digital camera.

15. The UV curing verification subsystem of claim 13 wherein the photometric device is a luminance meter.

16. The UV curing verification subsystem of claim 12 wherein the image data generator and the at least one source of visible light are on opposite sides of the ribbon to enable light from the at least one source of visible light to pass through the ribbon and be received by the image data generator.

17. The UV curing verification subsystem of claim 12 wherein the image data generator and the at least one source of visible light are positioned on a same side of the ribbon to enable light from the at least one source of visible light to be reflected from the ribbon into the image data generator.

18. The UV curing verification subsystem of claim 16 further comprising:
   a spool around which the ribbon is wrapped to enable the ribbon to be pulled from the spool as the spool rotates;
   a take-up reel;
   the member positioned to support the portion of the ribbon being between the spool and the take-up reel, a portion of the ribbon extending from the spool of ribbon to an end of the member and continuing to the take-up reel; and
   the image data generator and the at least one source of visible light being positioned on the same side of the ribbon between the end of the member and the take-up reel.

19. The UV curing verification subsystem of claim 17 further comprising:
   an actuator operatively connected to one of the imaging device and the UV curing verification subsystem, the actuator being configured to move the imaging device or UV curing verification subsystem operatively connected to the actuator between a first position that enables the image on the object to engage the ribbon and a second position that enables the at least one light source of the imaging device to illuminate the ribbon and the image data generator of the imaging device to generate image data of the ribbon.

20. The printing system of claim 9 wherein the image data generator is a radiometric device.

21. The UV curing verification subsystem of claim 19 wherein the image data generator is a radiometric device.

* * * * *